United States Patent [19]

Reynolds et al.

[11] Patent Number: 5,074,661
[45] Date of Patent: Dec. 24, 1991

[54] METHODS AND APPARATUS FOR RETROREFLECTIVE SURFACE INSPECTION AND DISTORTION MEASUREMENT

[75] Inventors: Rodger Reynolds; Donald A. Clarke; Timothy R. Pryor, all of Windsor, Ontario, Canada

[73] Assignee: Diffracto Ltd., Windsor, Canada

[21] Appl. No.: 212,011

[22] Filed: Jun. 27, 1988

Related U.S. Application Data

[63] Continuation-in-part of Ser. No. 33,930, Apr. 2, 1987, Pat. No. 4,863,268, which is a continuation of Ser. No. 711,646, Mar. 14, 1985, abandoned, and a continuation-in-part of Ser. No. 868,736, May 30, 1986, abandoned.

[51] Int. Cl.$^5$ ............................................. G01N 21/88
[52] U.S. Cl. ......................................................... 356/237
[58] Field of Search ........................... 350/105; 356/237

[56] References Cited

U.S. PATENT DOCUMENTS

| | | | |
|---|---|---|---|
| 1,998,054 | 4/1935 | McBurney | 350/105 X |
| 3,279,313 | 10/1966 | Kowalik et al. | 350/105 X |
| 3,702,213 | 11/1972 | Schwab | 350/105 |
| 4,863,268 | 9/1989 | Clarke et al. | 356/237 |

OTHER PUBLICATIONS

Bolhouse "Machine Vision Automates Inspection of Thick-Film Hybrids" IEEE Circuits & Devices Magazine, 2(1986) Jan., No. 1, pp. 44–48.

*Primary Examiner*—Vincent P. McGraw
*Attorney, Agent, or Firm*—Larson and Taylor

[57] ABSTRACT

Methods for improving and calibrating a retroreflection defects determination system are disclosed. The retroreflection system includes a light source which directs light to an area of a surface such that the light is reflected therefrom, a retroreflective member positioned such that the reflected light from the surface area impinges thereon and is thus returned to the surface area and re-reflected therefrom and an imaging device whereby the re-reflected light is imaged as a retroreflection image and scanned for intensity variations. In the identifying method, the retroreflective member of the system has a divergence angle, and the imaging step is repeated after the divergence angle has been appropriately changed. According to the calibrating methods, a first retroreflection image of a system is obtained. Then, one of the test conditions of the system is changed or the test surface is changed. The subsequent retroreflection image is then compared to the first in order to calibrate the system. A method for returning or calibrating the system to a previous condition is also disclosed. According to this method, a stored reference is displayed alternately and in quick succession on a visual display with a current image so that differences therebetween appear as a flicker. Then, the flickers are reduced by adjusting variables of the system and hence to return the system to the previous condition.

7 Claims, 3 Drawing Sheets

METHODS AND APPARATUS FOR RETROREFLECTIVE SURFACE INSPECTION AND DISTORTION MEASUREMENT

This application is a continuation in part of U.S. copending application, "D Sight TM Improvements" Ser. No. 33,930 filed Apr. 2, 1987 and now U.S. Pat. No. 4,863,268 which was a continuation of Ser. No. 711,646 filed Mar. 14, 1985, now abandoned, and "I Sight" Ser. No. 868,736 filed May 30, 1986 and now abandoned.

The present invention is directed at improvements that we have found in the method of producing enhanced surface images using retroreflective surface illumination and in the utilization of these images for practical measurement of surfaces.

In the following discussions, the term "Retroreflection Surface Image" (also called a "D Sight TM image") is utilized to describe the image produced when a light source illuminates a surface, and light from the surface strikes a myriad of small retroreflective elements, which reflect the light back to the surface and thence on reflection again from the surface, back to an observation point (or plane).

The image produced and discussed in the copending application "I Sight" is termed retroreflection index distortion image. A general term encompassing both types of images is "retroreflection image".

The principle inventions and improvements disclosed herein are:

1. The use of broad light sources (employing multiple elements or a single large element) to essentially flood the surface from different angles in order to eliminate certain disturbing effects.
2. The use of the same broadened light sources to enhance the apparent backlit image effect, thereby giving a correct position of the defect or distortion on the surface of the material.
3. The use of spatial optical modifiers to enhance sensitivity or for other purposes.
4. Selection or control of the retroreflector beamspread to modify or enhance the retroreflective surface image effect.
5. The use of sequential retroreflection, of particular use where infrared or other sources are used (where retroflector construction can be expensive).
6. Set up tools for test systems.

The invention is described in the following figures:

FIG. 1a illustrates a basic embodiment of the invention, FIG. 1b illustrates a portion of FIG. 1a on a larger scale, and FIG. 1c illustrates a distribution of retroreflected light, with FIGS. 1a-1c thus illustrating the effect of both "point" and broad light sources. The advantage offered by the broad light source in more realisticaly providing an image of the distortion of the object and in more accurately delineating the actual location of the distortion on the surface is discussed.

Incorporated by reference is a paper by Rodger Reynolds and Omer Hageniers, entitled "Optical Enhancement of Surface Contour Variations for Sheet Metal and Plastic Panel Inspection", presented at the SPIE International Symposium on Optical Engineering and Industrial Sensing for Advanced Manufacturing Technologies, Dearborn, Mich., June 28, 1988.

Figure 1A:
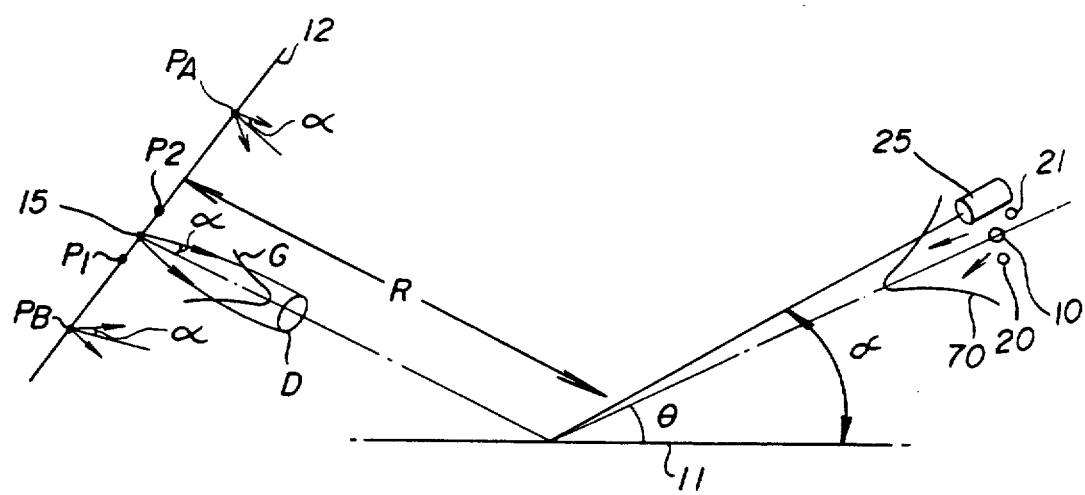
Figure 1B:
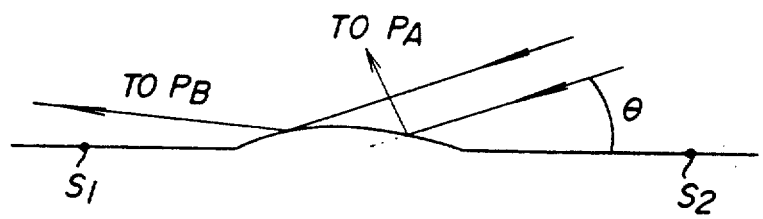
Figure 1C:
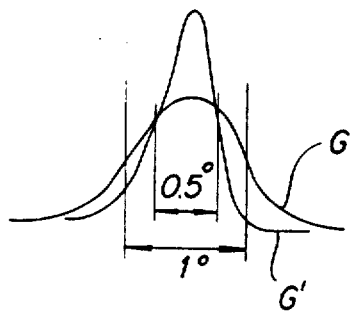

FIGS. 1a-1c illustrate creation of a retroreflection surface image and the generation of "primary" and "secondary" image signatures which are further described in the referenced paper by Reynolds and Hageniers.

Discussed here in more detail is the function of the three preferred types of light sources that have been found to date; point source, broad source, and a multiple collection of point sources effectively producing illumination of the surface from a plurality of angles like a broad source.

Consider the use of the "point" light source 10 which illuminates surface 11 with radiation which is reflected and then retroreflected by retroreflecting member (typically a screen) 12, containing a large number of small retroreflecting elements which are generally small relative to the extension of surface that is being measured (e.g. 50 micron diameter elements and surface areas 50 mm or more). The light returning from these elements e.g. those located at position 15, hits the surface again and is directed toward the camera which images the surface using the light so returned. The camera, 25, is shown in the "off-axis" ($\gamma \neq \theta$) position. It can also be "on-axis" ($\gamma = \theta$).

When a small up-dent (bump, protrusion, etc.) for example is present as shown in greater detail in FIG. 1b, the light from the sloped protuding portion of the surface is directed to other points (e.g. $P_A$, $P_B$) of the retroreflective screen than would normally have been illuminated by light reflected from that portion of the surface, had the surface not been distorted. The light from this and all portions of the screen returns in a cone D to the general region of the surface from whence it came, however covering an area generally larger than the up-dent, due to a typical divergence $a$ of $\pm \frac{1}{4}$ degree of returned light from the screen as shown by the gaussian distribution G (or G' for 0.25° elements) in FIG. 1c. In some cases, there may be little or no returned light realizing that if the slope of the up-dent is sufficiently great (relative to the screen extension), light (e.g. proceeding to point $P_A$) can completely exit the system (i.e. not able to hit the screen at all or at a suitable angle for retroreflection).

Importantly, the light that hits the generally undistorted surface near and surrounding the particular defect (e.g. at points $S_1$ and $S_2$), goes on to hit the screen (e.g. at points $P_1$ and $P_2$ in FIG. 1a), and in turn spreads in angle and re-radiates the surface, including the defect bump (or other distortion), creating a backlight (front light) effect, when $\gamma > \theta$.

Given a typical experimental setup, the beam spread $a$ of the retroelements is about $\pm \frac{1}{4}$ degree (to gaussian half power points), using 50-75 micron beads from Scotchlight 7615 by 3M Company). For screen to surface distances "R" on the order of 1-2 meters, actual area of the surface re-radiated by each minute retroelement, is relatively large compared to some of the typical defects of interest. A dirt pimple on sheet metal for example may be only 1 mm in diameter, whereas the diameter "D" on a zone on the surface reirradiated by each point on the screen is on the order of 50 mm at R=2 meters.

LIGHT SOURCE SIZE EFFECTS

At this point it is of interest to consider what happens using a "point" source of light small in extension relative to the surface. If one is looking directly at the retroreflective screen through the panel surface and the optical system is focused on the screen, one can see the various light and dark patterns made on the screen due to the redistribution of light caused by the distortion on the first reflection from the surface. For example an up-ding on the surface, that is a protrusion from the surface, creates a relatively dark zone on the screen, i.e. the light level that gets to the screen at the location that it would have, with no defect present, is reduced relative to its surroundings.

Using FIG. 1a as a reference, much of the light proceeds in the general direction of $P_A$ and $P_B$, with the dent functioning as a small convex mirror.

Conversely, an indentation into the surface at the same point on the surface can produce on the screen a concentration of light due to a "concave mirror" effect. The human visualizing the screen in reflection through the surface can see these light effects (which have, in the referenced technical paper, been called the "primary" signature of the distortion).

The primary signature of an up-ding for example, however appears to be shifted from the true location of the defect. It appears to lie farther from (or closer to) the observer depending on whether the light source is at a smaller (or larger) angle from the surface than the observer. The amount of displacement is proportional to the angular separation in the illumination and observation axes. For "off-axis" operation ($\gamma \neq \theta$), this makes it difficult to use the primary signature when one wants to determine a defect position on the surface (and say correct it using a grinder or whatever to grind off the area of defect, e.g. on a sheet metal panel).

Because of the pronounced bright/dark aspect of the primary image, the point source creates the sharpest contrast defect and makes the process of finding small defects of sharper slope easiest (at least where few other defects are present).

However, if one wishes to have the true contour image with positive slopes bright and negative slopes dark say, then a point light source generally should not be used. The same holds true in "off-axis" mode where one wishes to know accurately where on the panel the defect indication is from.

When one expands the light source size using either a single broad light source as in a camera flash (or larger), or a matrix of single bulbs such as 10, 20 and 21, it can be seen that the angle of attack to each defect on the surface is different from each point of each of the multiple sources (or an "infinite" number of points on the broad source). This being the case, any "primary signatures" on the screen, can be essentially "washed out" by the light coming to the screen from other undistorted surface locations (illuminated by other portions of the light source(s)), and little or no real "primary" effect on the screen is seen in looking through the panel at the screen.

When one focuses (especially with a camera lens which easily maintains a focus unlike the human eye) onto the test surface and looks at it under such broad source illumination, then one generally sees the secondary effect only, which appears to be a "backlighting" (for $\gamma > \theta$) of the defect from the light that did not hit the defect or other distortion on the surface. In this case, uniquely true appearing contour type patterns are produced, even for relatively larger slope defects. Sensitivity is however reduced for smaller defects due to the blurring of reradiated light from the screen caused by the multiple sources.

It should be noted that for a small slope defect where very little displacement occurs of the secondary and primary, one really sees only the secondary image anyway because the light power from it overwhelms that of the primary. Therefore, the main difference between the point source effect and the broad source is when the large slopes are present (such as caused by an up-ding 0.001" high and 0.020" in diameter). This also explains why when used with highlight oils and other things having certain ripple of substantial slope are used that this ripple is much more "noisy" when viewed with the point source than with a broad source. Again the broad source is preferable in these instances.

In terms of size for use on surfaces 1 meter square, typically a broad source consists of a group of 10 point light bulbs within a 5×10 cm area, or a camera flash gun of extension 2 cm×4 cm, where screen size is accordingly larger than the surface to intercept the reflected light therefrom. Smaller (larger) surfaces typically could use smaller (larger) broad sources and screens.

Let us consider the operation of the device through at least one theory. Again, light produced by a broad source 10 illuminates the surface area around the defect, and light reflected therefrom and rereflected by the retroreflector, reilluminates the defect and in essence provides the vast majority of the illumination of the defect which is observed by the camera. Light, on reflection once again by the surface, is directed to the camera, which in this example, is located on axis in a manner as shown (wherein beamsplitter 50 is used to direct light from the point source 51 along the viewing axis of camera 52).

Light from undistorted surface area such as $S_1$ and $S_1$ farther and farther away from the defect, contribute less and less actual light intensity to the defect because the beam spread from each of the small retroreflectors such as at position 15 is dying off both due to the area covered, due to the gaussian beam distribution from the individual small retroreflecting elements, and due to the angular divergence away from the camera from the defect.

This re-illumination of every point on the surface (and its distortion if any) from multiple points on the screen, produces what is termed in the reference paper, the "secondary image".

When one produces an image of the surface under such illumination, the positive slopes (viewed from the screen) direct light to (away from) the camera if the camera is farther in angle than the light source from the surface, the negative slopes do the opposite, and clearly the undistorted panel just continues to send the light back toward the source (albeit spread in cone of angle $\alpha$ which results in a) disc of light 70 at the plane of overlap, of gaussian distribution approximately 20–40 mm in diameter with the above experimental parameters. This disc is also related to Airy Diffraction Disc as it appears to be the far field diffraction pattern of the retroreflective elements. Most elements in any one screen are uniform in size, and in this case, diffraction rings are also observed.

Given the above, we may then consider the action of both on-axis and off-axis viewing. In the on-axis case, action of a protrusion defect is to shoot the light away from where it normally would have gone and the net effect is a darkening of the zone on the screen represented by the defect. The steeper the slope of the defect, the darker it appears.

In the off-axis case, the light from the defect directs (on reradiation by the multiple retroreflecting elements of the screen) either more or less light toward the camera depending on the slope of the defect, and whether it is positive or negative relative to the surrounding surface.

By mixing retroreflective element sizes and/or colors, one can soften the ring effect due to overlap of diffraction patterns. By changing sizes, wavelength or optical dispersion, one can change the sensitization of the technique.

For example, the increase in light by the camera due to positive slope of the defect is proportional to the slope, and the power densing which is in turn proportional to the gaussian beam spread, i.e. the angle $\alpha$. With larger element size or smaller wavelength, $\alpha$ will decrease and the sensitivity can typically increase with fixed diameter elements. A variable wavelength light source such as 51 controlled by light wavelength variable control 100 (e.g. a prism) can be used to change sensitivity, and to calibrate by using test surface samples of known surface slopes and observing the effects on wavelength needed to match the readings for example. These arguments also hold for index of refraction gradients in the copending "I Sight" case.

As another example, a retroreflective sheet comprised of corner cubes 0.1 mm in diameter were substituted for the typical 0.075 mm glass bead type screen (Scotchlight 7615). The gaussian disc at the observation location dropped from 10 cm in diameter to approximately 7.5 cm, and the sensitivity was noticed to improve. Sensitivity thus is improved by decreasing $\alpha$, until such condition as the diameter of retroreflected energy at the surface begins to approach the size of the feature of interest (e.g. a protrusion).

FIG. 3

Figure 3:
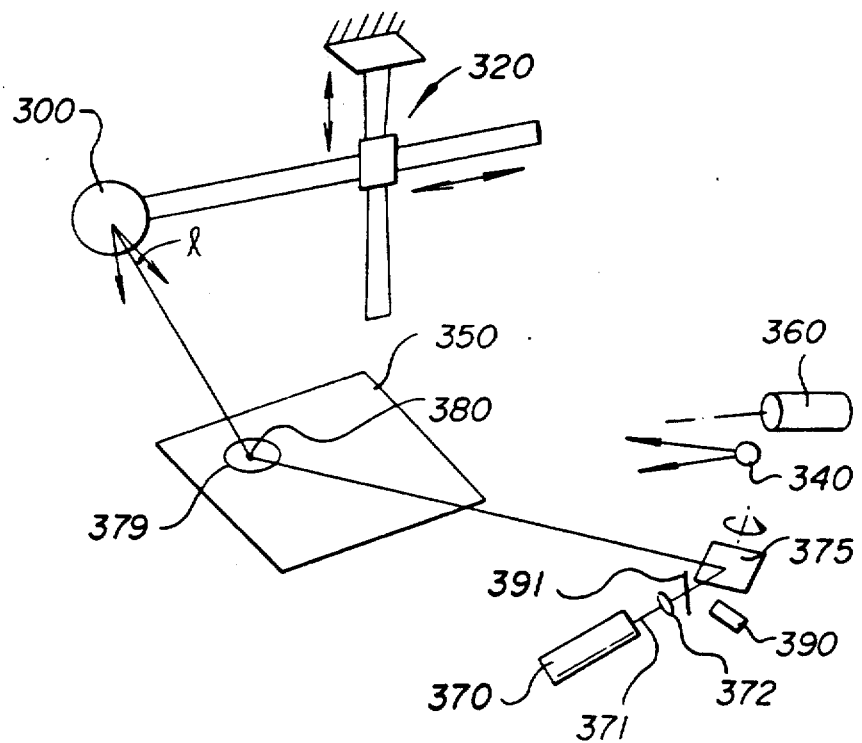
FIG. 3 illustrates an embodiment of the invention in which a retroreflective element grouping is moved through a light field illuminating a surface with the resultant retroreflective surface image accumulated by the camera or its memory (image summation optical or electronic).

FIG. 3 illustrates another embodiment of the invention wherein a reretroreflective surface image is built up sequentially, using a smaller group of retroreflective elements moved in space.

Figure 2:
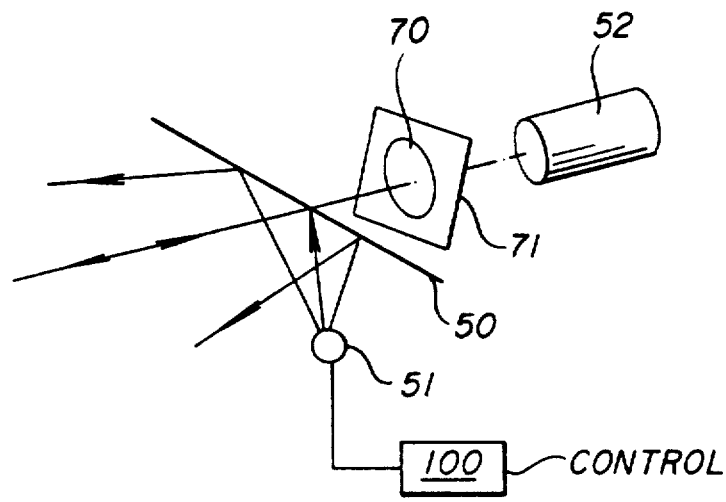
FIG. 2 illustrates further aspects of the operation of the invention and the effect of changing beamspread from various sizes of retroreflective elements.

If we consider the discussion relative to FIG. 2 concerning the theory of operation we can see that concerning any one defect, the predominant area which contributes to illumination of the defect is the area in the relative vicinity of the defect, and the corresponding effective zone of the screen. For a typical arrangement utilized to date for inspection of automotive panels, where the distances "R" and related retroreflection angles $\alpha$ are as discussed above, the rough area of the panel surface surrounding a small defect that is used at any one time to create the effect is let us say in the range of 50 mm–75 mm in diameter with a corresponding projection of this surface onto the screen.

Because of this, we can recreate the effect using a group of retroreflecting elements only large enough to effectively act on the light from the neighbouring effective areas of the surface (at any one time). For example, a 70 mm diameter disk 300 shown in FIG. 3 of retroreflective screen comprising a number of retroreflective elements is placed on the movable manipulator device 320, and moved through the reflected light field of source 340 from surface 350—time sequentially recreating the image on the camera which can be either stored in memory and added digitally there, or alternatively added optically simply by using the integration properties of the camera (e.g. a CCD).

By using a larger group of retroreflective elements (e.g. as in the previous screen), one doesn't require a manipulator. Thus this sequential technique is generally more complex, slower and of less utility. However, it does have the advantage that it allows the use of a plurality of high cost retroreflective elements that would simply be prohibitively expensive if they were used in a screen, larger in size than the test surface.

This would be the case particularly when one is using infrared radiation where specialized infrared retroreflectors are utilized (glass beads are thought to be generally ineffective beyond 2 microns).

The second reason, also of use particularly in the infrared is when one has to use a specialized light source such as a laser which tends to be cost effective only over a small area of illumination. Since the effect is localized to an area considerably larger than the defect but none the less relatively small relative to the surface of the panel, one can then also scan the light source (e.g. 370) having axis of illumination 371 by two axis mirror axis scanner 375, over the surface sequentially in unison with the scan of the retroreflector array. Precalculation, teaching, or servo control can be used to maintain the retroreflector array in the reflection field of the swept light beam.

A variant of FIG. 3 replaces the group of retroreflective elements 300, with a small number or even a single large aperture retroreflective element which is purposely chosen to have a beam spread (e.g. $= \alpha \frac{1}{2}$ degree) such that it covers an area of the surface (e.g. circle 379) substantially larger than the defect 380 for example and further has an aperture width wide enough to collect the light coming in from slightly divergent angles, not only from a point source, but from any broader sources chosen. A suitable single element retroreflector in the FIG. 3 example would be a 3 inch diameter corner cube with say 0.1–0.5 degree divergence, such a retroreflector would be much worse than the normal retroreflector of interest for other optical pursuits.

Finally, there is the possibility of using a "cloud" of individual retroreflective elements rather than elements fixed to a screen or manipulator for example. This may be the only way over very large surfaces, where an airplane could drop the elements as it passed over a surface or fluid (air, water) path whose gradient of shape or index of refraction was desired.

Figure 4:
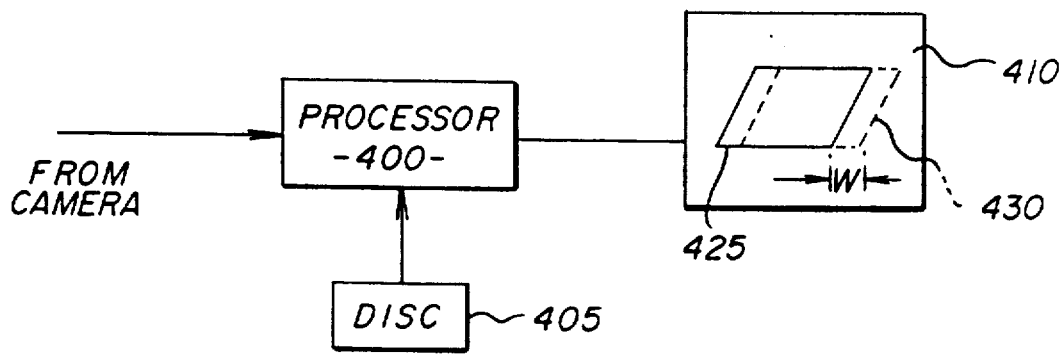
FIG. 4 illustrates apparatus according to the invention in which a stored reference retroreflective surface image of the object to be inspected, is alternately displayed on a monitor to assist in the correct repositioning of the test part and the adjustment of the light source and camera focus, optical magnification, or light intensity relationships.

Illustrated in FIG. 4 is a novel method for assisting operators to utilize the invention. It is often desirable to take a test part and position it back where an original master part for example had been, with the master part retroreflection surface image digitally stored on a disk 405 for example, used as a reference.

In comparing the test image to the master either by eye or through the use of a computer program, one wishes where possible to have the lens magnification/- the lens focal length, the lens aperture, light power, and the position of the part, all returned to the original situation used to obtain the master image for comparison.

It's noted that the master image in this case can be that of the same part taken at a different time or conversly a similar part known to be of high quality or what have you as a reference standard.

To do this the invention here comprises the alternate interlacing of image data from the master image to that of the instant image which causes a noticable flicker in the field where the two images do not correspond due to any of the variations mentioned above. As the variations are reduced a least flicker situation is obtained at which measurement is made.

To achieve this interlace, a frame grabber in processor 400 reads the master image from disk 405 and on alternate fields inserts the test image from camera 25 say.

Since there are a number of variables, there is a preferred way in which one goes about this. If the angle of incidence of the camera unit to the fixture is the same, we have found it preferable to:

1. Move the panel into rough location.
2. Adjust the camera zoom lens (if present) until the image appears to be the same size of that of the stored image.
3. Adjust the light power (easy to do due to a substantial flicker effect due to differing brightness levels of test and stored images).
4. Fine adjust the position of the panel to obtain the lens magnification. For example, in FIG. 4, the test panel image 425 would be moved a distance "W" to correspond with the stored image 430.

Other methods to achieve this have been considered including the simple presentation of the whole field of each image at a high flicker frequency rather than interlace.

It is further noted in FIG. 3 that the retroreflector group 300 can be square or other shapes beyond circular. Note too that the camera 360 can look at the whole surface simultaneously, or a camera such as 390 can be located (e.g. via beam splitter 391), so as to view a more limited area of the surface and swept together with the light source 370 (and optional lens 372) by mirror scanner or other sweeping means 375.

Figure 5A:
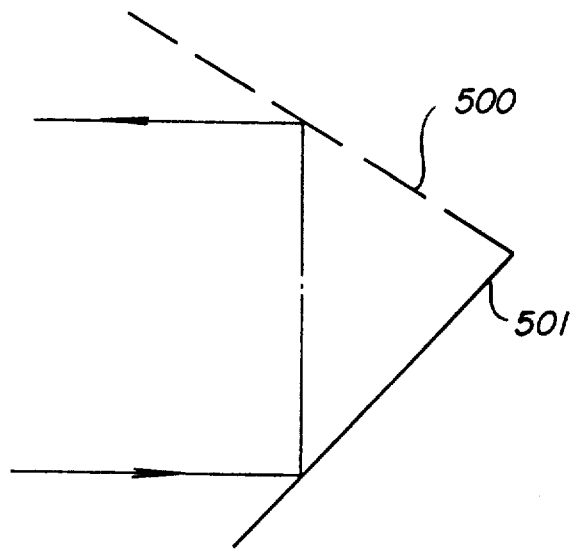
FIG. 5a is a schematic side view of a corner cube showing two faces and FIGS. 5b and 5c schematically depict side views of alternative faces.

A novel construction of a single retroreflector of suitable dispersion, usable for ultra violet, infra-red as well as visible wavelengths, is shown in FIG. 5a. In one version, a simple corner cube is made with at least one of its sides having a suitable dispersive surface. It should be noted that by having orthogonal sides of different dispersions one can achieve different $\alpha$ in different directions which may be useful in producing retroreflection images either using a single or plurality of retroreflective elements.

Figure 5B:
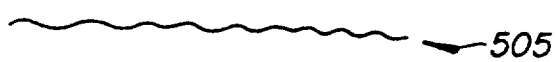
Figure 5C:
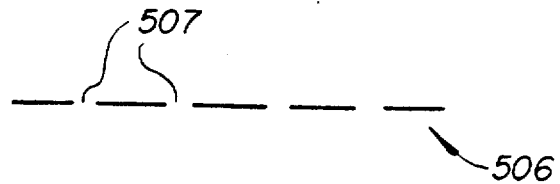

Corner cube type retroreflector 500 is constructed with at least one of its three reflective faces 501 having dispersive characteristics. This is achieved in this example by having an undulating form 505 as shown in FIG. 5B or the use of myriads of individual small diffractive elements such as holes 507 in aluminized side 506 as shown. It should be noted that these holes can be of a diameter on the order of the glass beads in screens used previously (e.g. 0.05–0.1 mm).

In the extreme, this retroreflector can be as large as the surface (or medium) to be imaged, thereby creating an alternate to the basic FIG. 1 arrangement. Lines rather than holes can also be used to create suitable dispersion due to diffraction.

Light in this invention means all electromagnetic wavelengths capable of being reflected and retroreflected, e.g. soft X-ray to millimeter wave.

What is claimed is:

1. A method for identifying various sizes of defects in a surface comprising the steps of:
    illuminating an area of a surface with light by directing light onto the surface area in such a manner that the light is reflected therefrom;
    providing a retroreflective member in a position such that the light reflected from the illuminated surface area impinges thereon, is then returned to the illuminated surface area in a cone having a divergence angle, and is re-reflected therefrom;
    imaging light re-reflected from the illuminated surface area;
    scanning the imaged light to determine intensity variations in that imaged light, and identifying from the intensity variations in the imaged light a defect in the surface; and
    repeating the above steps after the step of changing the divergence angle so that defects of a different size in the surface are easily identified.

2. A method for identifying defects as claimed in claim 1 wherein said changing step includes the step of changing the wavelength of the illumination light.

3. A method for identifying defects as claimed in claim 1 wherein said changing step includes the changing of the retroreflective member with another having a different divergence angle for reflected light.

4. A method for identifying defects as claimed in claim 1 and further including the step of comparing the imaged light from the illuminated surface before and after the changing step in order to identify defects of different sizes.

5. A method for calibrating a retroreflection image producing system, the system including a light source which directs light to an area of a surface such that the light is reflected therefrom, a retroreflective member positioned such that the reflected light from the surface area impinges thereon and is thus returned to the surface area and re-reflected therefrom, and an imaging device whereby the re-reflected light is imaged as a retroreflection image and scanned for intensity variations, said method comprising the steps of:
    producing a first retroreflection image of a test surface at a known set of test conditions of the system;
    changing at least one test condition of the system and hence providing a second set of test conditions;
    producing a second retroreflection image of the test surface at the second set of test conditions; and
    comparing the differences between the first and second retroreflection images to calibrate the system between the first and second sets of test conditions.

6. A method for calibrating a retroreflection image producing system, the system including a light source which directs light to an area of a surface such that the light is reflected therefrom, a retroreflective member positioned such that the reflected light from the surface area impinges thereon and is thus returned to the surface area and re-reflected therefrom, and an imaging device whereby the re-reflected light is imaged as a retroreflection image and scanned for intensity variations, said method comprising the steps of:
    producing a first retroreflection image of a test surface;

changing the test surface in a known manner to produce a second retroreflection image which should be changed from the first retroreflection image by an expected difference;

comparing the first and second retroreflection images to determine an actual difference; and comparing the actual difference with the expected difference to calibrate the system.

7. A method for recreating a previous retroreflective imaging condition with a retroreflection image producing system, the system including a light source which directs light to an area of a surface such that the light is reflected therefrom, a retroreflective member positioned such that the reflected light from the surface area impinges thereon and is thus returned to the surface area and re-reflected therefrom, and an imaging device whereby the re-reflected light is imaged as a retroreflection image, said method comprising the steps of:

producing a reference retroreflection image using a test surface;

storing the reference image in a storage means for a visual display;

subsequently producing a current retroreflection image of a surface at least substantially similar to the test surface;

displaying the reference image and the current image alternately in quick succession on the visual display so that any differences therebetween appear as a flicker in the visual display where the two images do not correspond; and adjusting variables of the system to reduce the flicker by changing the current image.

* * * * *